(12) United States Patent
Abe et al.

(10) Patent No.: US 7,737,214 B2
(45) Date of Patent: Jun. 15, 2010

(54) ADHESION PREVENTIVE MATERIAL

(75) Inventors: Yoshihiko Abe, Kanagawa (JP); Yutaro Sonoda, Kanagawa (JP); Jun Konishi, Kanagawa (JP); Takao Anzai, Kanagawa (JP); Miyuki Shimizu, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 10/592,956

(22) PCT Filed: Mar. 11, 2005

(86) PCT No.: PCT/JP2005/004311

§ 371 (c)(1),
(2), (4) Date: Jul. 25, 2007

(87) PCT Pub. No.: WO2005/087289

PCT Pub. Date: Sep. 22, 2005

(65) Prior Publication Data

US 2008/0058469 A1 Mar. 6, 2008

(30) Foreign Application Priority Data

Mar. 15, 2004 (JP) .............................. 2004-072887

(51) Int. Cl.
C08B 31/00 (2006.01)
C08B 37/00 (2006.01)
A01N 43/04 (2006.01)
A61K 31/715 (2006.01)

(52) U.S. Cl. ...................... 525/54.31; 525/54.3; 514/60

(58) Field of Classification Search ................ 525/54.3, 525/54.31; 514/60
See application file for complete search history.

(56) References Cited

U.S. PATENT DOCUMENTS

| | | | | |
|---|---|---|---|---|
| 4,360,635 | A * | 11/1982 | Alberts et al. ............. | 525/54.45 |
| 5,135,965 | A * | 8/1992 | Tahan ......................... | 523/106 |
| 5,470,843 | A * | 11/1995 | Stahl et al. .................... | 514/61 |
| 5,580,923 | A | 12/1996 | Yeung et al. | |
| 5,594,068 | A * | 1/1997 | Buchanan et al. .......... | 525/54.3 |
| 5,656,682 | A * | 8/1997 | Rimsa et al. .................. | 524/37 |
| 5,658,592 | A * | 8/1997 | Tanihara et al. ............. | 424/488 |
| 5,676,964 | A | 10/1997 | Della Valle et al. | |
| 5,858,994 | A * | 1/1999 | Kretzschmar et al. ......... | 514/62 |
| 5,906,997 | A | 5/1999 | Schwartz et al. | |
| 6,150,472 | A * | 11/2000 | Engbers ...................... | 525/404 |
| 6,312,725 | B1 * | 11/2001 | Wallace et al. .............. | 424/484 |
| 6,323,278 | B2 * | 11/2001 | Rhee et al. .................. | 525/54.1 |
| 6,630,457 | B1 * | 10/2003 | Aeschlimann et al. ........ | 514/54 |
| 6,734,298 | B1 | 5/2004 | Barbucci et al. | |
| 6,974,707 | B1 * | 12/2005 | Barie et al. .................. | 436/529 |
| 7,101,862 | B2 * | 9/2006 | Cochrum et al. .............. | 514/54 |
| 2002/0049281 | A1 * | 4/2002 | Zhao et al. .................. | 525/54.3 |
| 2003/0175327 | A1 * | 9/2003 | Cochrum et al. ............. | 424/445 |
| 2003/0199687 | A1 * | 10/2003 | Yalpani ....................... | 536/56 |
| 2004/0013626 | A1 * | 1/2004 | Gref et al. ................. | 424/70.13 |
| 2004/0072793 | A1 * | 4/2004 | Aeschlimann et al. ........ | 514/54 |
| 2004/0142016 | A1 * | 7/2004 | Luthra et al. ................. | 424/423 |
| 2004/0180993 | A1 * | 9/2004 | Shelton et al. ................ | 524/38 |
| 2004/0249066 | A1 * | 12/2004 | Heinzman et al. ........... | 525/54.3 |
| 2005/0065316 | A1 * | 3/2005 | Sikes ......................... | 528/322 |
| 2005/0079201 | A1 * | 4/2005 | Rathenow et al. ........... | 424/424 |
| 2005/0153429 | A1 * | 7/2005 | Liebmann-Vinson et al. ............ | 435/287.2 |
| 2005/0266086 | A1 * | 12/2005 | Sawhney ..................... | 424/486 |
| 2006/0178339 | A1 | 8/2006 | Abe et al. | |

FOREIGN PATENT DOCUMENTS

| | | |
|---|---|---|
| EP | 1 248 636 B1 | 7/2005 |
| JP | 2504163 T | 11/1990 |
| JP | 08-257111 A | 10/1996 |
| JP | 2853165 | 11/1998 |
| JP | 2000-116765 | 4/2000 |
| JP | 2002-511897 A | 4/2002 |
| JP | 2002-529549 T | 9/2002 |
| JP | 2003-520243 A | 7/2003 |
| JP | 2004-359895 A | 12/2004 |
| WO | WO 9707833 A2 * | 3/1997 |
| WO | WO00/27886 * | 5/2000 |
| WO | WO 2004/081055 A1 | 9/2004 |

OTHER PUBLICATIONS

Thornton, Melvin H. et al., "Clinical evaluation of 0.5% ferric hyaluronate adhesion prevention gel for the reduction of adhesions following peritoneal cavity surgery: open-label pilot study," Human Reproduction, vol. 13, No. 6, pp. 1480-1485 (1998).
Moberly, James B., et al., "Pharmacokinetics of icodextrin in peritoneal dialysis patients," Kidney International, vol. 62, Supplement 81, pp. S23-S33 (2002).

* cited by examiner

*Primary Examiner*—Mark Eashoo
*Assistant Examiner*—Liam J Heincer
(74) *Attorney, Agent, or Firm*—Buchanan Ingersoll & Rooney PC

(57) ABSTRACT

An adhesion preventive material including a cross-linking polysaccharide derivative containing at least one active ester group introduced in a polysaccharide side chain, which is capable of reacting with an active hydrogen-containing group, and being capable of forming a crosslinked material due to covalent binding among the active ester group and an active hydrogen-containing group upon contact with water under an alkaline condition, is disclosed. The adhesion preventive material is able to reduce preparation works to be carried out while previously estimating the time of application and does not require a special device.

13 Claims, No Drawings

ADHESION PREVENTIVE MATERIAL

TECHNICAL FIELD

The present invention relates to a crosslinking polysaccharide derivative which is to be used under a specific crosslinking condition and to an adhesion preventive material comprising a composition containing the subject polysaccharide derivative.

BACKGROUND ART

In a surgical operation, in the case where a biological tissue is invaded by operation works, adhesion occurs by inflammation during the process of tissue cure of that site, and normal actions of tissues or organs are hindered by the adhesion, thereby possibly producing a problem as a complication after the operation. For example, in an abdominal region, intestinal obstruction which is caused due to adhesion between an intestinal tract and a peritoneum after the operation is a critical complication.

For the purpose of preventing such adhesion after the operation from occurring, a bioabsorbable adhesion preventive material is sometimes used while expecting a barrier effect between tissues or organs.

As materials of adhesion preventive materials, there have hitherto been proposed, for example, a fibrous cellulose which is produced by microorganisms (Patent Document 1); a dry film of a polyion complex of an acidic polysaccharide containing an anionic group (a carboxyl group or a sulfonic group) and a basic polysaccharide containing a cationic group (an amino group) such as chitosan (Patent Document 2); a membrane of an intermacromolecular complex of a carboxyl-containing polysaccharide and a polyether (Patent Document 3); and an aqueous formulation containing polysaccharide dextrin (Patent Document 4).

Patent Document 1: Japanese Patent No. 2853165
Patent Document 2: JP-A-2000-116765
Patent Document 3: JP-A-2002-511897
Patent Document 4: JP-T-2003-520243

DISCLOSURE OF THE INVENTION

Problems that the Invention is to Solve

As described previously, in the adhesion preventive material, it is important that not only it meets clinical requirements, but also from the safety standpoint, it is designed so as to avoid risks as caused by using a non-biologically derived material, such as infectious diseases, to reduce toxicity of a component itself or its decomposition product as caused by using a synthetic material and to have biodegradation/absorption properties. In addition, it is desired that it is capable of reducing preparation works to be carried out while previously estimating the time of application during the operation and of quickly coping with the urgent application and does not require a special device in its use.

Means for Solving the Problems

An object of the invention is to provide a novel use method of a polysaccharide derivative as one capable of realizing an adhesion preventive material as required above. That is, the invention is aimed to provide an adhesion preventive material comprising a crosslinking material containing the subject polysaccharide derivative and further an adhesion preventive material which is simple in preparation works to be carried out while previously estimating the time of application and which does not require a special device.

Incidentally, as described previously, there have hitherto been made some proposals to utilize a polysaccharide for an adhesion preventive material. However, the use of an activated crosslinking polysaccharide in an uncrosslinked state has not been disclosed.

The object of the invention is attained by the following (1) to (35).

(1) An adhesion preventive material comprising a crosslinking polysaccharide derivative containing at least one active ester group introduced in a polysaccharide side chain, which is capable of reacting with an active hydrogen-containing group, and being capable of forming a crosslinked material due to covalent binding of the active ester group and an active hydrogen-containing group upon contact with water under an alkaline condition.

(2) The adhesion preventive material as set forth in (1), wherein the hydrogen active-containing group is a hydroxyl group in a polysaccharide molecule, and the polysaccharide derivative is self-crosslinking.

(3) The adhesion preventive material as set forth in (1) or (2), wherein the active hydrogen-containing group is an active hydrogen-containing group on the biological surface, and the polysaccharide derivative has adhesiveness to the biological surface.

(4) The adhesion preventive material as set forth in any one of (1) to (3), wherein the active ester group is an ester group in which an electrophilic group is bound to carbonyl carbon thereof.

(5) The adhesion preventive material as set forth in (4), wherein the electrophilic group is a group introduced from an N-hydroxyamine based compound.

(6) The adhesion preventive material as set forth in (1) to (5), wherein the active ester group is a succinimide ester group.

(7) The adhesion preventive material as set forth in any one of (1) to (6), wherein the polysaccharide derivative contains the active ester group in an amount of from 0.1 to 2 mmoles/g on the basis of the dry weight thereof.

(8) The adhesion preventive material as set forth in any one of (1) to (7), wherein the polysaccharide derivative further contains a carboxyl group and/or a carboxyalkyl group.

(9) The adhesion preventive material as set forth in any one of (1) to (8), wherein the polysaccharide derivative is of a non-salt type.

(10) The adhesion preventive material as set forth in any one of (1) to (9), wherein a raw material polysaccharide into which the active ester group is introduced is a polysaccharide which is soluble in an aprotic polar solvent at a temperature between 60° C. and 120° C. in a non-salt type thereof in a precursor stage of the crosslinking polysaccharide derivative containing a carboxyl group and/or a carboxyalkyl group.

(11) The adhesion preventive material as set forth in any one of (1) to (10), wherein the raw material polysaccharide into which the active ester group is introduced is a polysaccharide which contains neither a carboxyl group nor a carboxyalkyl group by itself.

(12) The adhesion preventive material as set forth in (11), wherein the raw material polysaccharide is at least one polysaccharide selected from the group consisting of dextran and pullulan.

(13) The adhesion preventive material as set forth in any one of (1) to (12), wherein the raw material polysaccharide is pectin and/or hyaluronic acid. This raw material polysaccharide is an active esterification precursor (acid group-containing polysaccharide) as it is.

(14) The adhesion preventive material as set forth in any one of (1) to (13), wherein the alkaline condition is in the pH range of from 7.5 to 12.

(15) The adhesive preventing material as set forth in any one of (1) to (14), which is in a powered state.

(16) The adhesion preventive material as set forth in any one of (1) to (14), which is an uncrosslinked sheet-like material.

(17) The adhesion preventive material as set forth in (16), wherein the sheet-like material is a heat dried film or a freeze dried sheet.

(18) An adhesion preventive material comprising a crosslinking polysaccharide composition containing (A) the crosslinking polysaccharide derivative as defined above in any one of (1) to (17) and (C) a polymer other than the polysaccharide derivative (A).

(19) The adhesion preventive material as set forth in (18), wherein the polymer (C) is a polymer containing two or more primary amino groups and/or thiol groups in one molecule.

(20) The adhesion preventive material as set forth in (18) or (19), wherein the polymer (C) is at least one member selected from a polyalkylene glycol derivative, a polypeptide, and a polysaccharide or a derivative thereof.

(21) The adhesion preventive material as set forth in (20), wherein the polyalkylene glycol derivative is at least one member selected from the group consisting of a polyethylene glycol (PEG) derivative, a polypropylene glycol derivative, polybutylene glycol derivative, and a block copolymer derivative or random copolymer derivative of polypropylene glycol and polyethylene glycol.

(22) The adhesion preventive material as set forth in (21), wherein the polyethylene glycol derivative has a basic polymer skeleton of at least one member selected from the group consisting of ethylene glycol, trimethylolethane, diglycerol, pentaerythritol, and hexaglycerol and has a molecular weight of from 100 to 50,000.

(23) The adhesion preventive material as set forth in (21), wherein the polyethylene glycol derivative is at least one member selected from the group consisting of an ethylene glycol type polyethylene glycol derivative having a thiol group in the both ends thereof and having a weight average molecular weight of 1,000, 2,000, 6,000 or 10,000; an ethylene glycol type polyethylene glycol derivative containing an amino group at the both ends thereof and having a weight average molecular weight of 1,000, 2,000, 6,000 or 10,000; a trimethylolethane type polyethylene glycol derivative having a thiol group in the three ends thereof and having a weight average molecular weight of 5,000 or 10,000; a trimethylolethane type polyethylene glycol derivative having an amino group in the three ends thereof and having a weight average molecular weight of 5,000 or 10,000; a dicylcerol type polyethylene glycol derivative having a thiol group in the four ends thereof and having a weight average molecular weight of 5,000, 10,000 or 20,000; a diglycerol type polyethylene glycol derivative having an amino group in the four ends thereof and having a weight average molecular weight of 5,000, 10,000 or 20,000; a pentaerythritol type polyethylene glycol derivative having a thiol group in the four ends thereof and having a weight average molecular weight of 10,000 or 20,000; a pentaerythritol type polyethylene glycol derivative having an amino group in the four ends thereof and having a weight average molecular weight of 10,000 or 20,000; a hexaglycerol type polyethylene glycol derivative having a thiol group in the eight ends thereof and a weight average molecular weight of 10,000 or 20,000; and a hexaglycerol type polyethylene glycol having an amino group in the eight ends thereof and having a weight average molecular weight of 10,000 or 20,000.

(24) The adhesion preventive material as set forth in (20), wherein the polypeptide is at least one member selected from collagen, gelatin, albumin, and polylysine.

(25) The adhesion preventive material as set forth in (20), wherein the polysaccharide is at least one member selected from pectin, hyaluronic acid, chitin, chitosan, carboxymethylchitin, carboxymethylchitosan, chondroitin sulfate, keratin sulfate, keratan sulfate, heparin, and derivatives thereof.

(26) The adhesion preventive material as set forth in any one of (18) to (25), which contains the crosslinking polysaccharide derivative (A) and the polymer (C) as a separate aqueous solution from each other.

(27) The adhesion preventive material as set forth in any one of (18) to (25), which is in a powdered state.

(28) The adhesion preventive material as set forth in any one of (18) to (25), which is an uncrosslinked sheet-like material.

(29) The adhesion preventive material as set forth in (28), wherein the sheet-like material is a composite sheet made of an uncrosslinked sheet of the polysaccharide derivative (A) having a sheet of the polymer (C) impregnated thereon.

(30) An adhesion preventive material comprising a crosslinking polysaccharide composition containing (A) the crosslinking polysaccharide derivative as defined above in any one of (1) to (17) and (B) a pH adjuster in a non-mixed state with the polysaccharide derivative (A).

(31) The adhesion preventive material as set forth in any one of (18) to (26), wherein the crosslinking polysaccharide composition further contains (B) a pH adjuster in a non-mixed state with the polysaccharide derivative (A).

(32) The adhesion preventive material as set forth in (26), wherein the aqueous solution of the polymer (C) contains the pH adjuster (B).

(33) The adhesion preventive material as set forth in (1) to (32), which is an aerosol or a paste.

(34) A kit containing the adhesion preventive material as set forth in (1) to (33).

(35) A method for preventing biological adhesion comprising making the adhesion preventive material as set forth in any one of (1) to (33) react in the presence of water in a desired site under an alkaline condition.

ADVANTAGES OF THE INVENTION

The crosslinking polysaccharide derivative according to the adhesion preventive material of the invention has essentially biological and chemical safety and is an excellent bioadaptive material because biologically derived materials and chemical substances having latent toxicity are not a skeleton of the derivative. Also, the subject crosslinking polysaccharide derivative exhibits self-crosslinking property and adhesiveness to the biological surface under an alkaline condition; it does not require a special device; it is easy for preparation at the time of application; its adhesiveness to the biological surface is sufficient; it is able to form a crosslinked material having excellent follow-up properties to an adherend and flexibility; and it is useful as an adhesion preventive material.

BEST MODES FOR CARRYING OUT THE INVENTION

The invention will be hereunder described in detail.
First of all, the crosslinking polysaccharide derivative according to the adhesion preventive material of the invention will be described. The crosslinking polysaccharide derivative contains at least one active ester group introduced in a polysaccharide side chain, which is capable of reacting with an active hydrogen-containing group. While a polysaccharide (raw material) into which this active ester group is introduced will be described later, since the polysaccharide molecule substantially contains a hydroxyl group by itself, namely it contains an active hydrogen-containing group, the polysaccharide derivative having an active ester group introduced into the subject polysaccharide contains both an active ester group and an active hydrogen-containing group in one molecular chain and exhibits a self-crosslinking property under a reaction condition. The "self-crosslinking property" as referred to herein means that the active ester group and the active hydrogen-containing group react with each other in one molecule or among molecules of the polysaccharide derivative, thereby forming covalent binding. Furthermore, in the case when the active hydrogen-containing group on the biological surface is utilized for the reaction, this crosslinking polysaccharide derivative exhibits adhesiveness to the biological surface.

In this description, such a crosslinking polysaccharide derivative may be sometimes called an active esterified polysaccharide and may be sometimes hereinafter referred to merely as a polysaccharide derivative.

Incidentally, the molecule regarding the "one molecular chain" or "in the molecule" as referred to herein means one of molecules as continuously bound to each other due to covalent binding.

The polysaccharide derivative according to the invention is an active esterified polysaccharide and substantially holds a polysaccharide skeleton. Accordingly, the polysaccharide derivative will be sometimes hereinafter described in a manner parallel to an active esterification method of a polysaccharide (production method of a polysaccharide derivative).

In the invention, as the active ester group which is introduced into the polysaccharide, any group may be employed so far as it is able to react with an active hydrogen-containing group in the presence of water under an alkaline condition to form covalent binding. Such an active ester group is a group which a polysaccharide molecule usually contains by itself or a group resulting from binding a strong electrophilic group as compared with usual esters to carbonyl carbon of a carboxyl group or methylcarboxyl group as introduced due to conversion into an acid type. Concretely, when this active ester group is expressed by "—COOX", it is preferable that the foregoing electrophilic group which forms an alcohol site "OX" is a group which is introduced from an N-hydroxyamine based compound. This is because since the N-hydroxyamine based compound is comparatively cheap raw material, it is easy to industrially introduce an active ester group.

Concretely, representative examples of the N-hydroxyamine based compound for the purpose of forming the foregoing "—OX" include N-hydroxysuccinimide, N-hydroxynorbornene-2,3-dicarboxylic acid imide, ethyl 2-hydroxyimino-2-cyanoacetate, 2-hydroxyimino-2-cyanoacetic acid amide, and N-hydroxypiperidine.

In the invention, the active ester group of the polysaccharide derivative may exist singly or in admixture of two or more kinds thereof.

Of these active ester groups, a succinimide ester group is preferable.

Though the polysaccharide derivative which is used in the invention contains at least one of the foregoing active ester groups in the molecule thereof, for the purpose of forming a crosslinking matrix, it usually contains two or more active ester groups in one molecule. Though the amount of the active ester group varies depending upon the use purpose, when expressed by an amount of the active ester group per gram of the dry weight thereof, it is preferably from 0.1 to 2 mmoles/g.

In the invention, the polysaccharide into which an active ester group is introduced and which constitutes a major skeleton of the polysaccharide derivative is not particularly limited so far as it contains two or more units of a monosaccharide structure in the major skeleton. Examples of such a polysaccharide include ones formed by covalent binding of a monosaccharide such as arabinose, ribose, xylose, glucose, mannose, galactose, fructose, sorbose, rhamnose, fucose, and ribodesose; a disaccharide such as trehalose, sucrose, maltose, cellobiose, gentiobiose, lactose, and melibiose; or a tri- or polysaccharide such as raffinose, gentianose, meleztose, and stachyose, and ones formed by further introducing a functional group into such a polysaccharide. In the invention, such a polysaccharide may be either a naturally existing material or an artificially synthesized material. Furthermore, the polysaccharide derivative according to the invention can be made up of a skeleton of a single polysaccharide or in admixture of two or more kinds thereof.

A weight average molecular weight of the polysaccharide which is the major skeleton of the polysaccharide derivative is not particularly limited. A polysaccharide having a weight average molecular weight of from 5,000 to 2,500,000, a value of which is corresponding to that of a material resulting from binding of several tens to several thousands of the foregoing monosaccharide, disaccharide or tri- or polysaccharide, is preferable. This is because in such a polysaccharide, not only the hardness of a gel after the polysaccharide derivative according to the invention has been crosslinked is readily adjusted, but also plural active ester groups and active hydrogen-containing groups are readily introduced in one molecular chain. A polysaccharide having a weight average molecular weight of from 10,000 to 1,000,000 is more preferable.

It is preferable that the raw material polysaccharide which forms the major skeleton of the polysaccharide derivative is a polysaccharide having the foregoing constitutional component and containing a carboxylic acid group for the purpose of forming an active ester group "—COOX" in the precursor stage of active esterification (this polysaccharide will be sometimes hereinafter referred to as an acid group-containing polysaccharide). The carboxylic acid group as referred to herein means a carboxyl group and/or a carboxyalkyl group (these will be sometimes hereinafter referred to as a carboxylic acid group). The carboxyalkyl group as referred to herein means a functional group in which a carboxyl group is bound to an alkyl skeleton, as enumerated by a carboxymethyl group, a carboxyethyl group, a carboxypropyl group, a carboxyisopropyl group, a carboxybutyl group, or the like.

The foregoing raw material polysaccharide is only required to be an acid group-containing polysaccharide in the precursor stage of the crosslinking polysaccharide derivative and may be either a natural polysaccharide containing a carboxylic acid group by itself or a polysaccharide in which a carboxyl group and/or a carboxyalkyl group is introduced into a polysaccharide which does not contain a carboxylic acid group by itself. Of these carboxylic acid group-containing polysaccharides, natural polysaccharides containing a carboxyl group, carboxylated polysaccharides having a carboxyl group introduced thereinto, carboxymethylated polysaccharides having a carboxymethyl group introduced thereinto, and carboxyethylated polysaccharides having a carboxyethyl group introduced thereinto are preferable. Natural polysaccharides containing a carboxyl group, carboxylated polysaccharides having a carboxyl group introduced thereinto, and carboxymethylated polysaccharides having a carboxymethyl group introduced thereinto are more preferable.

Though the foregoing natural polysaccharide containing carboxylic acid group by itself is not particularly limited, examples thereof include galacturonic acid-containing pectin and hyaluronic acid. For example, "GENUE pectin" of CP Kelco (Denmark) is exemplified as the pectin; "Hyaluronic Acid FCH" of Kibun Foods Inc. (Japan) is exemplified as the hyaluronic acid; and generally commercially circulated products can be utilized. Pectin is a polysaccharide containing galacturonic acid as the major component. Approximately 75 to 80% of pectin is made up of galacturonic acid, with other components being composed mainly of other saccharides. Pectin is a polysaccharide which is made up of galacturonic acid and other saccharides bound to each other in the foregoing proportion. Hyaluronic acid is used as an auxiliary for ophthalmic operation, a remedy for gonarthrosis, and so on. Hyaluronic acid does not contain galacturonic acid.

In the invention, it is desired that the carboxyl group and/or carboxyalkyl group of the polysaccharide derivative is of a "non-salt type" in which a salt is not coordinated, and it is desired that the ultimately obtained polysaccharide derivative is not in a salt form. The "salt" as referred to herein includes inorganic salts of an alkali metal, an alkaline earth metal, etc., quaternary amines such as tetra-butylammonium (TBA), and halogen salts such as iodochloromethyl pyridirium. The term "non-salt type" as referred to herein means that such a "salt" is not coordinated; and the term "not in a salt form" means that such a salt is not contained.

The foregoing polysaccharide into which a carboxyl group and/or a carboxyalkyl group is introduced is not particularly limited, and examples thereof include dextran and pullulan.

The foregoing dextran is used as a plasma substitute. "Dextran T fractions" of Amersham Biosciences K.K. (Japan) is exemplified as the dextran; and "Pullulan PI-20" of Hayashibara Biochemical Labs., Inc. (Japan) is exemplified as the pullulan. The pullulan is used as a medicinal additive including oral drugs, and ones which are less in biological contamination, such as endotoxin, are suitable.

In the invention, with respect to all of the polysaccharides, generally commercially circulated products can be utilized. The foregoing polysaccharides which have brought actual results in the medical applications are a polysaccharide which can be suitably utilized from the safety standpoint.

The carboxylation reaction of the polysaccharide can be carried out without particular limitations while utilizing a known oxidation reaction. Though the type of the carboxylation reaction is not particularly limited, examples thereof include dinitrogen tetroxide oxidation, fuming sulfuric acid oxidation, phosphoric acid oxidation, nitric acid oxidation, and hydrogen peroxide oxidation. In the respective reactions, the oxidation can be carried out by selecting a generally known reaction using a reagent. Each of the reaction conditions can be properly set up by an introduction amount of the carboxyl group. For example, it is possible to prepare a carboxylated polysaccharide (carboxylation material of polysaccharide) by suspending a polysaccharide which is the raw material in chloroform or carbon tetrachloride and adding dinitrogen tetrozide thereto, thereby oxidizing a hydroxyl group of the polysaccharide.

Furthermore, the carboxyalkylation reaction is not particularly limited, and a known carboxyalkylation reaction of polysaccharide can be utilized. Concretely, in the case of a carboxymethylation reaction, after alkalizing a polysaccharide, it is possible to select a reaction using monochloroacetic acid. Its reaction condition can be properly set up by an introduction amount of a carboxymethyl group.

In the invention, as a method for introducing a carboxylic acid group into the polysaccharide, any of the foregoing carboxylation or carboxyalkylation can be utilized without particular limitations. However, carboxyalkylation, especially carboxymethylation is suitable from the standpoints that a lowering of the molecular weight of the polysaccharide due to the introduction reaction of a carboxyl group is small and that an introduction amount of a carboxyl group is relatively easily controlled.

Furthermore, in the invention, the introduction of a carboxylic acid group is not particularly limited regarding the introduction into a polysaccharide not containing a carboxylic acid group by itself. A carboxyl group and/or a carboxymethyl group may further be introduced into a natural polysaccharide containing a carboxylic acid group by itself, for example, the foregoing hyaluronic acid.

In the active esterification of a carboxyl group and/or a carboxymethyl group of such an acid group-containing polysaccharide, the acid group-containing polysaccharide may be used singly or in admixture of two or more kinds thereof.

In the acid group-containing polysaccharide which is used for the active esterification, an amount of the carboxylic acid group per gram of its dry weight (on the assumption that the subject group is one molecule) is usually from 0.1 to 5 mmoles/g, preferably from 0.4 to 3 mmoles/g, and more preferably from 0.6 to 2 mmoles/g. When the proportion of this amount of the carboxylic acid group is less than 0.1 mmoles/g, there is often found the case where the number of an active ester group which is derived from the subject group and becomes a crosslinking point is insufficient. On the other hand, when the proportion of the amount of the carboxylic acid group exceeds 5 mmoles/g, the polysaccharide derivative (uncrosslinked) is sparingly soluble in a water-containing solvent.

The foregoing active esterification method of an acid group-containing polysaccharide (production method of a polysaccharide derivative) is not particularly limited. Examples thereof include a method of making the foregoing acid group-containing polysaccharide react with an electrophilic group introducing agent in the presence of a dehydration condensing agent; and a method of using an ester exchange reaction for introducing an active ester group into a polysaccharide from an active ester group-containing compound. Of these, the former method is suitable in the invention, and this method (also referred to as the method of the invention) will be mainly described below.

In carrying out the foregoing preferred method of the invention, in general, the foregoing acid group-containing polysaccharide is prepared into a solution of an aprotic polar solvent and provided for the reaction. More concretely, examples of the subject method include a method of carrying out a solution preparation step for dissolving a polysaccharide containing a carboxyl group or a carboxyalkyl group in an aprotic polar solvent and a reaction step for adding an electrophilic group introducing agent and a dehydration condensing agent to the subject solution, thereby subjecting the carboxyl group or carboxyalkyl group of the polysaccharide to active esterification; and a method of further carrying out a purification step and a drying step of the reaction product.

In the solution preparation step, dissolution of the polysaccharide in the aprotic polar solvent is achieved by adding the polysaccharide to the solvent and heating the mixture at from 60° C. to 120° C.

Accordingly, as the acid group-containing polysaccharide which is subjected to active esterification in this method, among the above-enumerated polysaccharides, those which are dissolved in the aprotic polar solvent at a temperature of from 60° C. to 120° C. are preferably used. Concretely, with respect to the polysaccharide which is used in the reaction for introducing an electrophilic group, it is preferable that the carboxyl group or carboxymethyl group is of an acid type in view of the solubility in the aprotic polar solvent. The "acid type" as referred to herein means that a counter cation species of the carboxyl group or carboxymethyl group is a proton. A polysaccharide containing a carboxyl group of an acid type is referred to as an acid type (raw material) polysaccharide. For example, pectin which is a carboxyl group-containing polysaccharide is referred to as acid type pectin. Carboxymethyl dextran containing a carboxymethyl group of an acid type is referred to as acid type carboxymethyl (CM) dextran (acid type CM dextran). In the "acid type", its counter cation species is a proton, and it is synonymous with the foregoing "non-salt type" from the standpoint that it is not in a salt form.

The "aprotic polar solvent" as referred to herein means a polar solvent which does not contain a proton capable of forming hydrogen binding with a nucleophilic agent containing an electrically positive functional group. The aprotic polar solvent which can be used in the production method according to the invention is not particularly limited, and examples thereof include dimethyl sulfoxide (DMSO), N,N-dimethylformamide, N-methyl-2-pyrrolidone, N,N-dimethylacetamide, and 1,3-dimethyl-2-imidazolidinone. Dimethyl sulfoxide can be suitably utilized because it has good solubility in a solvent for the polysaccharide.

In the reaction step, the carboxyl group and/or the carboxymethyl group of the polysaccharide is subjected to active esterification by adding an electrophilic group introducing agent and a dehydration condensing agent to an acid type polysaccharide solution. A reaction temperature at the time of active esterification is not particularly limited but is preferably from 0° C. to 70° C., and more preferably from 20° C. to 40° C. A reaction time varies with the reaction temperature and is usually from 1 to 48 hours, and preferably from 12 hours to 24 hours.

The "electrophilic group introducing agent" as referred to herein means a reagent for introducing an electrophilic group into the carboxyl group or carboxyalkyl group and converting it into an active ester group. The electrophilic group introducing agent is not particularly limited, and active ester derivable compounds which are used in many ways for the peptide synthesis can be utilized. Examples thereof include N-hydroxyamine based active ester derivable compounds. The N-hydroxyamine based active ester derivable compound is not particularly limited, and examples thereof include N-hydroxysuccinimide, N-hydroxynorbornene-2,3-dicarboxylic acid imide, ethyl 2-hydroxyimino-2-cyanoacetate, 2-hydroxyimino-2-cyanoacetic acid amide, and N-hydroxypiperidine. Of these, N-hydroxysuccinimide is more suitable because it has brought actual results in the peptide synthesis field and is readily commercially available.

In converting the carboxyl group or carboxyalkyl group into an active ester group by using an electrophilic group introducing agent, the "dehydration condensing agent" withdraws one water molecule which is produced by the condensation between the carboxyl group or carboxyalkyl group and the electrophilic group introducing agent, namely undergoes dehydration, thereby ester binding the both. The dehydration condensing agent is not particularly limited, and examples thereof include 1-ethyl-3-dimethylaminopropylcarbodiimide hydrochloride (EDC.HCl) and 1-cyclohexyl-(2-morphonyl-4-ethyl)-carbobodimide·meso-p-toluenesulfonate. Of these, 1-ethyl-3-dimethylaminopropylcarbodiimide hydrochloride (EDC.HCl) is more suitable because it has brought actual results in the peptide synthesis field and is readily commercially available.

In the purification step, after completion of the reaction step, the unreacted electrophilic group introducing agent and dehydration condensing agent and reaction by-products are removed from the reaction solution by means of usual reprecipitation, filtration and/or washing, or the like, whereby the polysaccharide derivative according to the invention can be obtained.

In the drying step, for the purpose of removing the washing solvent from the polysaccharide derivative obtained in the foregoing purification step, drying may be carried out in a usually employed method.

In the invention, as described previously, it is preferable that an amount of the active ester group of the polysaccharide derivative is finally from 0.1 to 2 mmoles/g. In the above, it is possible to control the introduction amount of the active ester group into the carboxyl group of the active esterified raw material saccharide so as to obtain such a polysaccharide derivative.

In order to control the introduction amount of the active ester group, in the foregoing reaction step, it is possible to adjust a mixing amount of the electrophilic group introducing agent and the dehydration condensing agent. Concretely, it is preferable that a ratio (Z/X) of the molar number (Z mmoles) of the dehydration condensing agent to the molar number (X mmoles) of the total carboxyl groups of the saccharide is an addition condition which meets the relationship of $0.1<Z/X<50$ at the foregoing reaction temperature. This is because when Z/X is less than 0.1, the addition amount of the dehydration condensing agent is small so that the reaction efficiency is low, whereby a desired rate of introduction of the active ester group is hardly achieved, whereas when Z/X is more than 50, the addition amount of the dehydration condensing agent is large so that though a rate of introduction of the active ester group is high, the resulting polysaccharide derivative is hardly dissolved in water.

The molar number (Y mmoles) of the electrophilic group introducing agent to the molar number (X mmoles) of the total carboxyl groups of the polysaccharide is not particularly limited so far as the electrophilic group introducing agent is added in an amount of the reaction amount or more in response to the rate of introduction of the active ester group. It is preferable that the addition condition meets the relationship of $0.1<Y/X<100$.

Even after the active ester group has been introduced, in general, the polysaccharide derivative according to the invention contains a hydroxyl group contained in a glucopyranose ring in the saccharide skeleton molecule and therefore, contains an active hydrogen-containing group by itself. However, the active hydrogen-containing group in the molecule is not limited thereto, and the polysaccharide derivative according to the invention may further contain an active hydrogen-containing group which is introduced into the molecule as the need arises. In this case, the active hydrogen-containing group may be of a single kind or in admixture of two or more kinds thereof.

The polysaccharide derivative according to the invention can widely contain functional groups such as known elements and atomic groups in addition to the foregoing active ester group and active hydrogen-containing group so far as the characteristics of the invention are not hindered.

Specific examples of such a functional group include halogen elements such as fluorine, chlorine, bromine, and iodine;

a carboxyl group; carboxyalkyl groups such as a carboxymethyl group, a carboxyethyl group, a carboxypropyl group, and a carboxyisopropyl group; a silyl group; an alkylenesilyl group; an alkoxysilyl group; and a phosphoric acid group. Such a functional group may be introduced singly or in admixture of two or more kinds thereof.

The rate of introduction of the active ester group can be expressed by multiplication of a ratio (AE/TC) of the molar number (AE) of the active ester group content in the resulting polysaccharide derivative to the molar number of the carboxyl group and the molar number of the carboxymethyl group contained in the active esterified raw material polysaccharide (hereinafter expressed as the total carboxyl groups (TC)) by 100.

The rate of introduction of the active ester group can be determined by, for example, a method as described in *Biochemistry*, Vol. 14, No. 7 (1975), pages 1535 to 1541.

In particular, a carboxyl group and/or a carboxymethyl group contained in the raw material polysaccharide remaining in the case where the active ester group is introduced in a rate of introduction of the active ester group of less than 100% may be contained.

The "crosslinking structure" as referred to herein means that covalent binding is formed in a single molecular chain and/or among plural molecular chains of the polysaccharide derivative according to the invention and as a result, the molecular chain of the polysaccharide derivative takes a reticular three-dimensional structure. According to this crosslinking, the active ester group and the active hydrogen-containing group can be bound in one molecular chain, but covalent binding may be formed among plural molecules, thereby achieving crosslinking. Prior to the crosslinking forming reaction, the polysaccharide derivative according to the invention which is soluble in water forms a crosslinking structure with a progress of the reaction, and its fluidity is lowered to form a water-insoluble block (hydrated gel), whereby a polysaccharide crosslinked material is formed. In particular, when a property such that a crosslinking structure can be formed by covalent binding in an own molecular chain or among molecular chains without using other crosslinking agent is defined as "self-crosslinking property", the saccharide derivative according to the invention is a self-crosslinking polysaccharide.

Furthermore, not only the polysaccharide derivative according to the invention is self-crosslinking due to participation of the intramolecular active hydrogen-containing group as described previously, but also when applied to the biological surface, the subject polysaccharide derivative is able to exhibit adhesiveness to the biological surface due to the reaction between the active hydrogen-containing group and the active ester group on the biological surface. Such a use embodiment is a preferred embodiment of the polysaccharide derivative according to the invention. Incidentally, at the time of applying on the biological surface, as a matter of course, self-crosslinking may be generated at the same time.

In the invention, the active hydrogen-containing group which participates in the reaction with the active ester group is not particularly limited so far as it is a group capable of forming covalent binding upon reaction with the foregoing active ester group under a reaction condition as specified in the invention. In the invention, groups which are exemplified as a general active hydrogen-containing group may be employed. Specific examples thereof include a hydroxyl group, an amino group, and a thiol group. Here, the amino group includes a primary amino group and a secondary amino group. Above all, the case where the active hydrogen-containing group is a hydroxyl group or a primary amino group is preferable because the reactivity with the active ester group is good and the time until it is crosslinked and gelled is short.

In the invention, the foregoing crosslinking reaction of the polysaccharide derivative is based on the formation of covalent binding due to the reaction between the active ester group and the active hydrogen-containing group. Concretely, examples thereof include a method of providing a polysaccharide derivative in the presence of water, steam, a water-containing solvent, or the like under an alkaline condition, thereby achieving crosslinking; and a method of crosslinking the polysaccharide derivative by adding a pH adjustor in a solution of a polysaccharide derivative, thereby achieving crosslinking.

More concretely, it is possible to crosslink a polysaccharide derivative by providing it in the presence of water at a pH of from 7.5 to 12, and preferably from 9.0 to 10.5. On that occasion, when the pH of water is lower than 7.5, the self-crosslinking property is low so that a sufficient degree of crosslinking is not obtained. On the other hand, the application of water having a pH of higher than 12 is not suitable from the physiological standpoint while the crosslinking agent proceeds.

In the invention, the "alkaline condition" refers to a condition under which water having a pH of at least 7.5 is present. In the crosslinking polysaccharide derivative according to the invention, since contribution of heat to the crosslinking reaction is not substantially large, the temperature of the "alkaline condition" is not particularly limited but, for example, can be made to fall within the range of from 10° C. to 40° C.

The "contact with water under an alkaline condition" as referred to herein means that a polysaccharide derivative is brought into contact with water in a form of an alkaline condition, thereby putting the polysaccharide derivative under an alkaline condition. In the case where the form of the polysaccharide derivative is a powder, it is possible to add water which has been previously adjusted under an alkaline condition or to add water in a state that a power of a polysaccharide derivative and a pH adjustor are mixed. In the case where the form of the polysaccharide derivative is an aqueous solution, it is possible to add water which has been previously adjusted under an alkaline condition or to add a pH adjustor. The polysaccharide derivative is put under an alkaline circumstance due to these works so that the crosslinking reaction starts. That is, when the polysaccharide derivative comes into contact with water under an alkaline condition, its crosslinking reaction starts and proceeds. Accordingly, the pH of a mixture of water under an alkaline condition and the polysaccharide derivative may be an alkaline condition but may be not always an alkaline condition. When the polysaccharide derivative comes into contact with water under an alkaline condition, the formation of crosslinking is started; the crosslinking reaction is not substantially started by UV (ultraviolet light) or heating; and the formation of crosslinking does not substantially proceed by UV or heating.

The adhesion preventive material according to the invention can provide an adhesion preventive material made up of only it while utilizing the matter that the foregoing polysaccharide derivative is self-crosslinking.

The polysaccharide derivative as an adhesion preventive material can be used in a powered material or sheet-like material form. That is, a powered polysaccharide derivative can be obtained by crushing or pulverizing the polysaccharide derivative obtained by the foregoing synthesis reaction and optionally performing the particle size adjustment to adjust the particle size range. In order to make the particle size small, there are no particular limitations, and freeze dry pulverization, mill pulverization and/or classification may be employed. After crushing or pulverization, the resulting powdered material can be adjusted to an arbitrary particle size distribution by sieving. An average particle size is not particularly limited but is preferably from several tens nm to several hundreds μm. The resulting powered material can be prepared into a paste-like material or an aerosol by a usually employed method.

The sheet-like polysaccharide derivative can be produced by a solution preparation step for dissolving a polysaccharide derivative in water and a drying step for heat drying or freeze drying after spreading the subject solution in a desired shape. Concretely, the sheet-like polysaccharide derivative can be obtained by preparing an aqueous solution having a polysaccharide derivative dissolved therein and freeze drying it. At the time when the sheet-like polysaccharide derivative is prepared, a pH of water for preparing the aqueous solution is preferably from 3.0 to 7.5. This is because when the pH is less than 3.0, the resulting sheet exhibits strong acidity, whereas when it is more than 7.5, the active ester group may possibly be liberated. The heat dried sheet can be obtained by spreading the foregoing aqueous solution onto a substrate and heat drying it at from 30 to 110° C. If desired, the heat drying can be carried out under a reduced pressure. The freeze dried sheet can be obtained by freezing the foregoing aqueous solution and drying it while freezing. If desired, a usual freeze dryer can be used.

Furthermore, in the invention, an adhesion preventive material in a form of a crosslinking polysaccharide composition comprising a combination of the foregoing polysaccharide derivative (A) and other component (hereinafter often abbreviated as a composition or a polysaccharide composition) is provided, too. Though the other component varies depending upon its kind, it may form a composition in a state coming into contact with the polysaccharide derivative or may be in a non-contact state until mixing at the time of application. Concretely, for example, an adhesion preventive material comprising a composition containing the foregoing polysaccharide derivative (A) and a pH adjuster (B) is provided.

The pH adjuster (B) may be fed without being mixed or may be mixed in advance. Though the timing of mixing is not particularly limited, it is before or during the use and is properly selected. If desired, the foregoing composition containing the polysaccharide derivative (A) and the pH adjuster (B) may contain other substance. The other substance may be mixed with the polysaccharide derivative or may not be mixed with it.

The pH adjuster (B) which is used in the invention means an aqueous solution for adjusting the polysaccharide derivative or polysaccharide composition according to the invention at a pH of from 7.5 to 12, a water-containing solvent, or a salt (powder), or the like. The pH adjuster (B) is not particularly limited, and specific examples thereof include a sodium hydrogencarbonate aqueous solution or power, a phosphoric acid based buffer solution (for example, disodium hydrogenphosphate and potassium dihydrogenphosphate), and an acetic acid-ammonia based buffer solution. Above all, sodium hydrogencarbonate can be suitably used from the safety standpoint by utilizing it as a medical pH adjuster in a form of an intravenous injection of its about 7% aqueous solution (pH 8.3).

Examples of the form of the foregoing composition include a two-component system of an aqueous solution having a concentration of the polysaccharide derivative of from 1 to 80% (w/v) and water whose pH is separately kept at from 7.5 to 10.5.

According to this system, by mixing the both at the time of application, it is possible to prepare a mixed aqueous solution having a final concentration of the polysaccharide of from 0.1 to 60% (w/v). There is also enumerated a mixed aqueous solution prepared by adding a salt of the pH adjuster (B) to an aqueous solution of the polysaccharide derivative having a concentration of from 1 to 80% (w/v) at the time of application and mixing while dissolving so as to have a final concentration of the polysaccharide derivative of from 0.1 to 80% (w/v). For the mixing, though a usual mixing method can be selected, it is preferred to carry out mixing until the mixing state becomes uniform to an extent that the desired reaction proceeds.

A crosslinking polysaccharide composition containing the polysaccharide derivative (A) and other polymer (C) is also provided as an adhesion preventive material. The polymer (C) is used for the purpose of adjusting hardness of a hydrated gel when crosslinking the polysaccharide composition and its properties. The foregoing polysaccharide composition may contain one kind or two or more kinds of the polysaccharide derivative (A). Furthermore, this composition may contain the foregoing pH adjuster (B).

Though the polymer (C) is not particularly limited, it is preferred to use one containing two or more of a primary amino group, a thiol group or a hydroxyl group in one molecule of the polymer (C). Specific examples of the polymer (C) include polyalkylene glycol derivatives, polypeptides, and polysaccharides or derivatives thereof. Though the content of the polymer (C) in the polysaccharide composition according to the invention is not particularly limited, it is preferable that the polymer (C) is blended in an amount of from 5 to 50% by weight based on the whole of the polysaccharide composition. Incidentally, the polymer (C) can be used singly or in admixture of two or more kinds thereof.

Examples of the foregoing polyalkylene glycol derivative include polyethylene glycol (PEG) derivatives, polypropylene glycol derivatives, polybutylene glycol derivatives, and polypropylene glycol-polyethylene glycol block copolymer derivatives or random copolymer derivatives. Then, examples of the basic polymer skeleton of the polyethylene glycol derivative include ethylene glycol, diglycerol, pentaerythritol, and hexaglycerol. A molecular weight of the polyalkylene glycol derivative is preferably from 100 to 50,000, and more preferably from 1,000 to 20,000.

The foregoing polyethylene glycol derivative is not particularly limited, and examples thereof include ethylene glycol type polyethylene glycol derivatives containing a thiol group at the both ends thereof and having a weight average molecular weight of 1,000, 2,000, 6,000 or 10,000; ethylene glycol type polyethylene glycol derivative containing an amino group at the both ends thereof and having a weight average molecular weight of 1,000, 2,000, 6,000 or 10,000; trimethylolethane type polyethylene glycol derivatives containing a thiol group at the three ends thereof and having a weight average molecular weight of 5,000 or 10,000; trimethylolethane type polyethylene glycol derivatives containing an amino group at the three ends thereof and having a weight average molecular weight of 5,000 or 10,000; diglycerol type polyethylene glycol derivatives containing a thiol group at the four ends thereof and having a weight average molecular weight of 5,000, 10,000 or 20,000; diglycerol type polyethylene glycol derivatives containing an amino group at the four ends thereof and having a weight average molecular weight of 5,000, 10,000 or 20,000; pentaerythritol type polyethylene glycol derivatives having a thiol group at the four ends thereof and having a weight average molecular weight of 10,000 or 20,000; pentaerythritol type polyethylene glycol derivatives having an amino group at the four ends thereof and having a weight average molecular weight of 10,000 or 20,000; hexaglycerol type polyethylene glycol derivatives containing a thiol group at the eight ends thereof and having a weight average molecular weight of 10,000 or 20,000; and hexaglycerol type polyethylene glycol derivatives containing an amino group at the eight ends thereof and having a weight average molecular weight of 10,000 or 20,000.

The "weight average molecular weight" as referred to herein is one of numeral values expressing an average molecular weight of a polymer. A polymer is a mixture of molecules having the same basic structural unit and a different molecular length (chain length) and therefore, has a molecular weight distribution corresponding to the difference of the molecular chain length. In order to express that molecular weight, an average molecular weight is employed. Though the average molecular weight includes a weight average molecular weight and a number average molecular weight, the weight average molecular weight is employed herein. Incidentally, in the invention, a value (100%) of the weight average molecular weight includes one whose upper limit is 110% and one whose lower limit is 90%. The polyethylene glycol derivative can be prepared in accordance with, for example, a method as described in Chapter 22 of *Poly(ethylene Glycol) Chemistry: Biotechnical and Biomedical Applications*, edited by J. Milton Harris, Plenum Press, NY (1992). In addition, the polyethylene glycol derivative can be chemically modified so as to contain one or plural primary amino groups or thiol groups. Furthermore, such a material can be purchased from NOF Corporation as a polyethylene glycol derivative (for example, SUNBRIGHT HGEO-20TEA and SUNBRIGHT PTE-10TSH).

The foregoing polypeptide is not particularly limited, and examples thereof include collagen, gelatin, albumin, and polylysine. The polysaccharide is not particularly limited, and examples thereof include pectin, hyaluronic acid, chitin, chitosan, carboxymethyl chitin, carboxymethyl chitosan, chondroitin sulfate, keratin sulfate, keratan sulfate, heparin, and derivatives thereof.

In the polysaccharide composition containing the polysaccharide derivative (A) and the polymer (C), suitable combinations of the polysaccharide derivative (active esterified polysaccharide) (A) and the polymer (C) are as follows. Incidentally, in these combinations, a shape thereof (for example, a sheet-like form, a powdered form, and a liquid form) can be properly selected while referring to the working examples as described later.

A combination of at least one polymer (C) selected from the group consisting of an ethylene glycol type PEG derivative containing a thiol group at the both ends thereof, an ethylene glycol type PEG derivative containing an amino group at the both ends thereof, a trimethylolethane type PEG derivative containing a thiol group at the three ends thereof, a trimethylolethane type PEG derivative containing an amino group at the three ends thereof, a pentaerythritol type PEG derivative containing a thiol group at the four ends thereof, a pentaerythritol type PEG derivative containing an amino group at the four ends thereof, a hexaglycerol type PEG derivative containing a thiol group at the eight ends thereof, a hexaglycerol type PEG derivative containing an amino group at the eight ends thereof, albumin, gelatin, collagen, polylysine, pectin, chitosan, chitin, and carboxymethyl(CM) chitin, with active esterified pectin.

A combination of at least one polymer (C) selected from the group consisting of an ethylene glycol type PEG derivative containing a thiol group at the both ends thereof, an ethylene glycol type PEG derivative containing an amino group at the both ends thereof, a trimethylolethane type PEG derivative containing a thiol group at the three ends thereof, a trimethylolethane type PEG derivative containing an amino group at the three ends thereof, a pentaerythritol type PEG derivative containing a thiol group at the four ends thereof, a pentaerythritol type PEG derivative containing an amino group at the four ends thereof, a hexaglycerol type PEG derivative containing a thiol group at the eight ends thereof, a hexaglycerol type PEG derivative containing an amino group at the eight ends thereof, albumin, gelatin, collagen, polylysine, pectin, chitosan, chitin, and CM chitin, with active esterified CM dextran.

A combination of at least one polymer (C) selected from the group consisting of an ethylene glycol type PEG derivative containing a thiol group at the both ends thereof, an ethylene glycol type PEG derivative containing an amino group at the both ends thereof, a trimethylolethane type PEG derivative containing a thiol group at the three ends thereof, a trimethylolethane type PEG derivative containing an amino group at the three ends thereof, a pentaerythritol type PEG derivative containing a thiol group at the four ends thereof, a pentaerythritol type PEG derivative containing an amino group at the four ends thereof, a hexaglycerol type PEG derivative containing a thiol group at the eight ends thereof, a hexaglycerol type PEG derivative containing an amino group at the eight ends thereof, albumin, gelatin, collagen, polylysine, pectin, chitosan, chitin, and CM chitin, with active esterified CM pullulan.

A combination of at least one polymer (C) selected from the group consisting of an ethylene glycol type PEG derivative containing a thiol group at the both ends thereof, an ethylene glycol type PEG derivative containing an amino group at the both ends thereof, a trimethylolethane type PEG derivative containing a thiol group at the three ends thereof, a trimethylolethane type PEG derivative containing an amino group at the three ends thereof, a pentaerythritol type PEG derivative containing a thiol group at the four ends thereof, a pentaerythritol type PEG derivative containing an amino group at the four ends thereof, a hexaglycerol type PEG derivative containing a thiol group at the eight ends thereof, a hexaglycerol type PEG derivative containing an amino group at the eight ends thereof, albumin, gelatin, collagen, polylysine, pectin, chitosan, chitin, and CM chitin, with active esterified CM hydroxyethyl starch.

A combination of at least one polymer (C) selected from the group consisting of an ethylene glycol type PEG derivative containing a thiol group at the both ends thereof and having a weight average molecular weight of 1,000, 2,000, 6,000 or 10,000, an ethylene glycol type PEG derivative containing an amino group at the both ends thereof and having a weight average molecular weight of 1,000, 2,000, 6,000 or 10,000, a trimethylolethane type PEG derivative containing a thiol group at the three ends thereof and having a weight average molecular weight of 5,000 or 10,000, a trimethylolethane type PEG derivative containing an amino group at the three ends thereof and having a weight average molecular weight of 5,000 or 10,000, a diglycerol type PEG derivative containing a thiol group at the four ends thereof and having a weight average molecular weight of 5,000, 10,000 or 20,000, a diglycerol type PEG derivative containing an amino group at the four ends thereof and having a weight average molecular weight of 5,000, 10,000 or 20,000, a pentaerythritol type PEG derivative having a thiol group at the four ends thereof and having a weight average molecular weight of 10,000 or 20,000, a pentaerythritol type PEG derivative having an amino group at the four ends thereof and having a weight average molecular weight of 10,000 or 20,000, a hexaglycerol type PEG derivative containing a thiol group at the eight ends thereof and having a weight average molecular weight of 10,000 or 20,000, and a hexaglycerol type PEG derivative containing an amino group at the eight ends thereof and having a weight average molecular weight of 10,000 or 20,000, with active esterified pectin.

A combination of at least one polymer (C) selected from the group consisting of an ethylene glycol type PEG derivative containing a thiol group at the both ends thereof and having a weight average molecular weight of 1,000, 2,000, 6,000 or 10,000, an ethylene glycol type PEG derivative containing an amino group at the both ends thereof and having a weight average molecular weight of 1,000, 2,000, 6,000 or 10,000, a trimethylolethane type PEG derivative containing a thiol group at the three ends thereof and having a weight average molecular weight of 5,000 or 10,000, a trimethylolethane type PEG derivative containing an amino group at the three ends thereof and having a weight average molecular weight of 5,000 or 10,000, a diglycerol type PEG derivative containing a thiol group at the four ends thereof and having a weight average molecular weight of 5,000, 10,000 or 20,000, a diglycerol type PEG derivative containing an amino group at the four ends thereof and having a weight average molecular weight of 5,000, 10,000 or 20,000, a pentaerythritol type PEG derivative having a thiol group at the four ends thereof and having a weight average molecular weight of 10,000 or 20,000, a pentaerythritol type PEG derivative having an amino group at the four ends thereof and having a weight average molecular weight of 10,000 or 20,000, a hexaglycerol type PEG derivative containing a thiol group at the eight ends thereof and having a weight average molecular weight of 10,000 or 20,000, and a hexaglycerol type PEG derivative containing an amino group at the eight ends thereof and having a weight average molecular weight of 10,000 or 20,000, with active esterified CM dextran.

A combination of at least one polymer (C) selected from the group consisting of an ethylene glycol type PEG derivative containing a thiol group at the both ends thereof and having a weight average molecular weight of 1,000, 2,000, 6,000 or 10,000, an ethylene glycol type PEG derivative containing an amino group at the both ends thereof and having a weight average molecular weight of 1,000, 2,000, 6,000 or 10,000, a trimethylolethane type PEG derivative containing a thiol group at the three ends thereof and having a weight average molecular weight of 5,000 or 10,000, a trimethylolethane type PEG derivative containing an amino group at the three ends thereof and having a weight average molecular weight of 5,000 or 10,000, a diglycerol type PEG derivative containing a thiol group at the four ends thereof and having a weight average molecular weight of 5,000, 10,000 or 20,000, a diglycerol type PEG derivative containing an amino group at the four ends thereof and having a weight average molecular weight of 5,000, 10,000 or 20,000, a pentaerythritol type PEG derivative having a thiol group at the four ends thereof and having a weight average molecular weight of 10,000 or 20,000, a pentaerythritol type PEG derivative having an amino group at the four ends thereof and having a weight average molecular weight of 10,000 or 20,000, a hexaglycerol type PEG derivative containing a thiol group at the eight ends thereof and having a weight average molecular weight of 10,000 or 20,000, and a hexaglycerol type PEG derivative containing an amino group at the eight ends thereof and having a weight average molecular weight of 10,000 or 20,000, with active esterified CM pullulan.

A combination of at least one polymer (C) selected from the group consisting of an ethylene glycol type PEG derivative containing a thiol group at the both ends thereof and having a weight average molecular weight of 1,000, 2,000, 6,000 or 10,000, an ethylene glycol type PEG derivative containing an amino group at the both ends thereof and having a weight average molecular weight of 1,000, 2,000, 6,000 or 10,000, a trimethylolethane type PEG derivative containing a thiol group at the three ends thereof and having a weight average molecular weight of 5,000 or 10,000, a trimethylolethane type PEG derivative containing an amino group at the three ends thereof and having a weight average molecular weight of 5,000 or 10,000, a diglycerol type PEG derivative containing a thiol group at the four ends thereof and having a weight average molecular weight of 5,000, 10,000 or 20,000, a diglycerol type PEG derivative containing an amino group at the four ends thereof and having a weight average molecular weight of 5,000, 10,000 or 20,000, a pentaerythritol type PEG derivative having a thiol group at the four ends thereof and having a weight average molecular weight of 10,000 or 20,000, a pentaerythritol type PEG derivative having an amino group at the four ends thereof and having a weight average molecular weight of 10,000 or 20,000, a hexaglycerol type PEG derivative containing a thiol group at the eight ends thereof and having a weight average molecular weight of 10,000 or 20,000, and a hexaglycerol type PEG derivative containing an amino group at the eight ends thereof and having a weight average molecular weight of 10,000 or 20,000, with active esterified CM hydroxyethyl starch.

A mixing ratio (SD/AP) of the polysaccharide derivative (SD) (A) to the polymer (C) (AP) is preferably from 20/80 to 98/2 (w/w). This is because when the polymer (C) is mixed in an amount of more than 80% by weight, the self-crosslinking property of the polysaccharide (A) is hardly obtained due to hindrance of the polymer (C), whereas when it is mixed in an amount of less than 2% by weight, the hardness and properties of the finally obtained hydrated gel are hardly adjusted.

An adhesion preventive material comprising the foregoing polysaccharide composition can be provided in a desired form such as a sheet-like form, a powdered form, and a liquid form. A powdered polysaccharide composition can be prepared by mixing the powered polymer (C) with the foregoing powdered polysaccharide derivative (A). Furthermore, a powdered polysaccharide composition containing a salt of a pH adjuster can be prepared by mixing a powdered salt of a pH adjuster with the foregoing powdered polysaccharide composition.

A granulated material can be prepared by granulating the foregoing powdered polysaccharide composition or the foregoing powdered polysaccharide composition containing a salt of a pH adjuster; and a sheet or a plate can be prepared by pressure welding the foregoing powdered polysaccharide composition or the foregoing powdered polysaccharide composition containing a salt of a pH adjuster. A sheet-like polysaccharide composition can be obtained by attachment of the polymer (C) in a powdered form or impregnation of the polymer (C) by a coating method on a heat dried sheet or freeze dried sheet of the foregoing polysaccharide derivative (A). The "impregnation" as referred to herein refers to a state that when the polymer (C) is impregnated on the surface of the sheet, the polymer (C) covers the sheet surface. In the case where the sheet is of a porous structure, the "impregnation" refers to a state that the polymer (C) covers the sheet surface and the inner surfaces of pores inside the sheet.

A two-part type can be formed by preparing an aqueous solution of the polysaccharide derivative (A) and an aqueous solution of the polymer (C), respectively. By mixing these aqueous solutions, it is possible to prepare a hydrated gel made up of the polysaccharide (A) and the polymer (C). At this time, the aqueous solution of the polysaccharide derivative (A) preferably has a concentration of from 1 to 80% (w/v), and the aqueous solution of the polymer (C) preferably has a concentration of from 1 to 80% (w/v). In particular, the water for dissolving the polymer (C) therein may be water as prepared so as to have a pH of from 7.5 to 10.5, or a salt of a pH adjuster may be added at the time of mixing by using pure water or a buffer solution. It is suitable that after mixing the aqueous solution of the polysaccharide derivative (A) and the aqueous solution of the polymer (C), a final concentration of the sum of the polysaccharide derivative (A) and the polymer (C) is from 0.1 to 80% (w/v).

The sheet-like polysaccharide composition can be crosslinked by providing it in the presence of water. On that occasion, the foregoing pH adjuster can be used as the water. The pH adjuster is preferably an aqueous solution having a pH of from 7.5 to 10.5. The pH adjuster may be attached in a powdered form to the sheet-like polysaccharide composition.

The sheet-like polysaccharide composition is formed by dissolving the polysaccharide derivative (A) in water and spreading the subject solution in a desired shape and drying it, followed by an impregnation step for impregnating the polymer (C) on the resulting sheet-like material of the polysaccharide derivative (A). In the foregoing impregnation step, the polymer (C) and a solution containing a non-aqueous volatile organic solvent are impregnated on the sheet-like material and dried, whereby the polymer (C) can be impregnated without hindering the shape of the surface of the sheet-like polysaccharide derivative (A). Incidentally, the "non-aqueous volatile organic solvent" as referred to herein means an organic solvent which is incompatible with water and volatizes. The non-aqueous volatile organic solvent is not particularly limited, and examples thereof include chloroform and dichloromethane.

In the invention, the dosage form of the adhesion preventive material is not particularly limited, and examples thereof include a liquid form, a sheet-like form, a powdered form, a paste, and an aerosol.

The polysaccharide derivative or polysaccharide composition as an adhesion preventive material can be used by spreading in a desired shape as described previously.

The polysaccharide composition containing the polymer (C) can be used by further mixing with the foregoing pH adjuster. In mixing the polysaccharide composition with the pH adjuster, the both may be previously mixed (premixed) or may be properly mixed on the spot at the time of use. By adding an aqueous solution such as a pH adjuster at the time of use, it is possible to apply the adhesion preventive material to a desired local site.

Furthermore, the polysaccharide composition can further contain widely known additives within the range where the characteristics of the invention are not hindered. On that occasion, in particular, it is preferred to use a biologically acceptable additive. The additive is not particularly limited, and examples thereof include a hardening catalyst, a filler, a plasticizer, a softening agent, a stabilizer, a dehydrating agent, a coloring agent, an anti-sagging agent, a thickener, a physical property adjuster, a reinforcing agent, a thixotropic agent, an anti-degrading agent, a flame retarder, an antioxidant, an ultraviolet light absorber, a pigment, a solvent, a carrier, an excipient, an antiseptic, a binder, a swelling agent, an isotonic agent, a dissolution aid, a preservative, a buffering agent, and a diluent. These additives can be contained singly or in admixture of two or more kinds thereof.

Specific examples of the additive include water, physiological saline, pharmaceutically acceptable organic solvents, gelatin, collagen, polyvinyl alcohol, polyvinylpyrrolidone, carboxyvinyl polymers, sodium carboxymethyl cellulose, poly(sodium acrylate), sodium alginate, water-soluble dextran, sodium carboxymethyl starch, pectin, methyl cellulose, ethyl cellulose, xanthan gum, gum arabic, tragacanth, casein, agar-agar, diglycerine, propylene glycol, polyethylene glycol, vaseline, paraffin, stearyl alcohol, stearic acid, human serum albumin (HAS), mannitol, sorbitol, lactose, PBS, nonionic surfactants, biodegradable polymers, serum-free media, surfactants which are tolerable as medical additives, and biologically acceptable physiological pH buffer solutions.

The carrier to be used is selected properly or in combination among the foregoing materials depending upon the use site but is not limited thereto. Furthermore, pharmaceutical formulations such as aerosols and pastes can be prepared by using a suitable propellant.

The adhesion preventive material of the invention can be provided as a kit containing the foregoing pH adjuster while taking into consideration convenience at the time of use. In the adhesion preventive material, the polysaccharide derivative (A), the polysaccharide composition and/or the pH adjuster can be contained in a state that they are not mixed with each other in a packing or a package together with or separately from the adhesion preventive material. The package may contain other constitutional material which can be used as an adhesion preventive material.

The polysaccharide derivative or polysaccharide composition can be included in a state containing or not containing an aqueous solution or a powdered pH adjuster therein in a kit in a powdered, sheet-like or aqueous solution form.

The "adhesion preventive material" as referred to herein means a substance which is used for the purpose of preventing the adhesion in a biological adhesion preventive site or in the vicinity thereof, and is made up of a safe component which is low in biologically noxious toxicity and is biologically tolerable. The adhesion preventive material may be either biodegradable or non-biodegradable. Preferably, the adhesion preventive material is biodegradable.

By applying the adhesion preventive material in a targeted site and optionally covering a site at which the adhesion occurs or a site at which occurrence of the adhesion is expected, the adhesion is inhibited so that an adhesion preventing effect is revealed. The adhesion preventive material is applied to a targeted site, and other desired site is adhered. Thereafter, the adhesion preventive material is fixed, allowed to stand or press bonded, followed by elapsing a certain period of time. On that occasion, a fixing tool or the like can be used.

In the invention, there is provided a method for preventing biological adhesion comprising bringing an adhesion preventive material into contact with a desired site in the presence of water. The contact with a desired site is achieved by blowing, filling or coating a powdered adhesion preventive material. In the case of a sheet-like adhesion preventive material, the contact is achieved by sticking, filling, covering, press bonding or standing it. In the case of a liquid adhesion preventive material, the contact is achieved by coating, spraying, dropping, painting or plastering it. The biological adhesion prevention can be carried out by these measures.

The polysaccharide derivative which is used as the adhesion preventive material is a polysaccharide containing an active ester group and an active hydrogen-containing group in one molecular chain and capable of forming a crosslinking structure upon covalent binding between the subject active ester group and the subject active hydrogen-containing group. When the polysaccharide derivative is used as an adhesion preventive material, since it meets the clinical requirements, does not utilize a biologically derived material from the safety standpoint and is made up of a natural or artificial saccharide as the major skeleton, risks of infectious diseases or the like can be avoided. Since toxicity of the component itself or a degradation product thereof is low and the polysaccharide constitutes the major skeleton, the material is designed so as to have a biodegradable absorption property.

Furthermore, since the polysaccharide derivative which is used in the invention is small in preparation works to be carried out while previously estimating the time of application so that it is able to rapidly adapt a sudden application and does not require a special device in using it, anyone can simply use it. Then, since the polysaccharide derivative can be provided solely or as a polysaccharide composition containing it, it is applicable to wide and various use methods. The polysaccharide composition does not hinder characteristics of the polysaccharide derivative having the foregoing characteristics.

In addition, the polysaccharide derivative and polysaccharide composition can be processed into various shapes including a powdered form, a sheet-like form, and a granular form and can be used for different purposes depending upon the purpose. With respect to the method of producing this polysaccharide derivative or polysaccharide composition, since it is only required to mix necessary reagents and heat them, a special device or the like is not required so that the method is simple. In view of the foregoing characteristics, the polysaccharide derivative and its composition according to the invention are suitable as an adhesion preventive material.

The invention will be more specifically described below with reference to the following Examples. However, these are exhibited merely as one example, and it should be construed that the invention is not limited thereto in any way.

EXAMPLES

Synthesis Example 1

(1) Preparation of Raw Material Polysaccharide (Acid Type Polysaccharide)

Carboxymethyl dextran (acid type CM dextran) as a raw material polysaccharide, which is a raw material of an active esterified polysaccharide derivative, was prepared.

125 g of a 18% (w/v) sodium hydroxide aqueous solution (sodium hydroxide, manufactured by Wako Pure Chemical Industries, Ltd.) was added to 10 g of dextran (Dextran T-40, manufactured by Amersham Biosciences K.K., weight average molecular weight: 40,000), and the mixture was stirred at 25° C. for 90 minutes. Subsequently, 75 g of a 20% (w/v) monochloroacetic acid aqueous solution (monochloroacetic acid, manufactured by Wako Pure Chemical Industries, Ltd.) was added, and the mixture was stirred at 60° C. for 6 hours. Thereafter, the reaction solution was adjusted so as to have a pH of 1.0 by using 20% hydrochloric acid and then stirred at 25° C. for 2 hours. The reaction solution was added dropwise to 5 L of a 90% by volume ethanol aqueous solution (100% ethanol, manufactured by Wako Pure Chemical Industries, Ltd.), and a deposit was recovered by using a suction funnel. A deposit as obtained by using 3 L of a 90% by volume ethanol aqueous solution was washed and finally purged with ethanol, followed by drying in vacuo. There was thus prepared acid type CM dextran.

(2) Determination of Carboxyl Group or Carboxymethyl Group

With respect to the acid type CM dextran (raw material polysaccharide) as obtained above in (1), the determination of a carboxyl group or a carboxymethyl group contained therein was carried out. 0.2 g (A (g)) of the raw material polysaccharide was weighed and added to a mixed solution of 20 mL of a 0.1 moles/L sodium hydroxide aqueous solution and 10 mL of an 80% by volume methanol aqueous solution, and the mixture was stirred at 25° C. for 3 hours. Three drops of a 1.0% (w/v) phenolphthalein/90% by volume ethanol aqueous solution as an indicator was added to the resulting solution, and acid-base back titration was carried out by using 0.05 moles/L sulfuric acid, thereby measuring a use amount ($V_1$ mL) of the 0.05 moles/L sulfuric acid (phenolphthalein, manufactured by Wako Pure Chemical Industries, Ltd.). Furthermore, a use amount ($V_0$ mL) of the 0.05 moles/L sulfuric acid was measured at a blank which was carried out in the same manner except for not adding the raw material saccharide. An amount (B mmoles/g) of a carboxyl group and a carboxymethyl group in the raw material saccharide was calculated according to the following numerical expression (1) and found to be 1.01 mmoles/g. Incidentally, both the 0.1 moles/L sodium hydroxide aqueous solution and the 0.05 moles/L sulfuric acid as used had a strength of 1.00.

$$B=(V_0-V_1)\times 0.1 \div A \qquad (1)$$

A: Weight (g) of raw material polysaccharide

B: Amount (mmoles/g) of carboxyl group and carboxymethyl group (3) Preparation of Active Esterified CM Dextran For an active esterification reaction of the acid type CM dextran, DMSO as a reaction solvent, N-hydroxysuccinimide (NHS) (manufactured by Wako Pure Chemical Industries, Ltd.) as an electrophilic group introducing agent and 1-ethyl-3-dimethylaminopropylcarbodiimide hydrochloride (EDC) (manufactured by Wako Pure Chemical Industries, Ltd.) as a dehydration condensing agent were used, thereby preparing an active esterified polysaccharide (polysaccharide derivative).

2.0 g of the acid type CM dextran (amount of carboxymethyl group: 1.01 mmoles/g) as obtained above in (2) was added to 200 g of DMSO, and the mixture was stirred for dissolution at 70° C. for 3 hours. Thereafter, 2.32 g (20.2 mmoles) of NHS and 3.86 g (20.2 mmoles) of EDC were added, and the mixture was stirred at 25° C. for 24 hours. The reaction solution was added dropwise to 2 L of anhydrous acetone, and a deposit was recovered by using a suction funnel. A deposit as obtained by using 1 L of anhydrous acetone was washed and dried in vacuo. There was thus prepared active esterified CM dextran. Z/X and Y/X ratios are as follows.

$$Z/X=10, Y/X=10$$

(4) Calculation of Introduction Amount of NHS in Active Esterified Polysaccharide (Polysaccharide Derivative)

With respect to the active esterified CM dextran as obtained in (3), an introduction amount of NHS as obtained in the following manner was 0.4 mmoles/g.

The introduction amount of NHS is the content of NHS present per unit weight of the polysaccharide derivative.

In order to prepare a calibration curve of N-hydroxysuccinimide (NHS), NHS standard aqueous solutions of 0.1, 0.2, 0.5, 1.0 and 2.5 mM were prepared, respectively. 0.2 mL of a 2N sodium hydroxide aqueous solution was added to 1 mL of each of the NHS standard aqueous solutions, and the mixture was heated at 60° C. and stirred for 10 minutes. After allowing to it stand for cooling, 1.5 mL of 0.85 N sulfuric acid and 0.5 mL of a 0.5% $FeCl_3$/1 N hydrochloric acid solution were added, and an absorbance at an absorption wavelength of 500 nm was measured by using a spectrophotometer ($FeCl_3$, manufactured by Wako Pure Chemical Industries, Ltd.). A concentration and an absorbance of each of the NHS aqueous solutions were plotted on the X-axis and the Y-axis, respectively, and linear approximation was carried out, thereby obtaining the following numerical expression (2) for calculating an NHS concentration.

$$Y = \alpha X + \beta \quad (2)$$

X: NHS concentration (mM)

Y: Absorbance at wavelength of 500 nm

α=0.178 (gradient)

β=0.021 (intercept)

r=0.995 (correlation function)

An NHS concentration X (mM) is calculated on the basis of the absorbance.

Next, 0.01 g (C (g)) of the active esterified polysaccharide of (3) was weighed and added to 1 mL of pure water, and the mixture was stirred at 25° C. for 3 hours. Thereafter, 0.2 mL of a 2 N sodium hydroxide aqueous solution was added, and the mixture was heated at 60° C. and stirred for 10 minutes. After allowing it to stand for cooling to room temperature, 1.5 mL of 0.85 N hydrochloric acid was added. After removing insoluble matters from the resulting solution containing the insoluble matters by using filter cotton, 0.5 mL of a 0.5% $FeCl_3$/1 N hydrochloric acid solution was added, and an absorbance at an absorption wavelength of 500 nm was measured by using a spectrophotometer ($FeCl_3$, manufactured by Wako Pure Chemical Industries, Ltd.). When a measured value of absorbance exceeds the absorbance at the time when the concentration of the NHS standard solution is 5 mM, dilution with pure water was carried out (dilution ratio, H). The content of the NHS group (D mmoles) in the active esterified polysaccharide was calculated from a measured value of absorbance by utilizing the foregoing numerical expression (2) for calculating the NHS concentration. Subsequently, an introduction amount of NHS in the active esterified polysaccharide was determined according to the following numerical expression (3).

$$\text{Introduction amount of } NHS \text{ (mmoles/g)} = (D \times H) \times 0.001/C \quad (3)$$

(5) Self-crosslinking Property of Active Esterified Polysaccharide Derivative

It was confirmed from the following test that the active esterified polysaccharide as obtained above is self-crosslinking. 0.2 g of the active esterified polysaccharide was weighed in a cleaned test tube having a capacity of 10 mL (LARBO LT-15100, manufactured by Terumo Corporation), to which was then added 1 mL of pure water, followed by mixing. Next, 1 mL (pH: 8.3) of an 8.3% (w/v) sodium hydrogencarbonate aqueous solution (sodium hydrogencarbonate, manufactured by Wako Pure Chemical Industries, Ltd.) as a pH adjuster was added, followed by mixing at about 2,000 rpm for about one minute by using a test tube mixer (MT-31, manufactured by Yamato Scientific Co., Ltd.). The state of contents of the test tube was visually confirmed before and after the mixing. Thus, in the active esterified CM dextran, the contents in the test tube after mixing were a block-like material (hydrated gel) so that the active esterified CM dextran was judged to be "self-crosslinking".

Synthesis Example 2

(1) Preparation of Raw Material Polysaccharide (Acid Type Polysaccharide)

Carboxymethylhydroxyethyl starch (acid type CM hydroxyethyl starch) as a raw material polysaccharide, which is a raw material of an active esterified polysaccharide derivative, was prepared.

The preparation was carried out under a condition exactly the same as in Synthesis Example 1(1), except for using hydroxyethyl starch (COATMASTER, manufactured by Sansho Co., Ltd., weight average molecular weight: 200,000) in place of the dextran as used in Synthesis Example 1(1).

(2) Determination of Carboxyl Group or Carboxymethyl Group

The determination was carried out in the same manner as in the case of acid type CM dextran as described in Synthesis Example 1(2).

An amount of the carboxymethyl group of the acid type CM hydroxyethyl starch as obtained in Synthesis Example 2(1) was 0.72 mmoles/g.

(3) Preparation of Active Esterified CM Hydroxyethyl Starch

For an active esterification reaction of the acid type CM hydroxyethyl starch, the same reaction solvent, electrophilic group introducing agent and dehydration condensing agent as in Synthesis Example 1(3) were used, thereby preparing an active esterified saccharide.

2.0 g of the acid type CM hydroxyethyl starch (amount of carboxymethyl group: 0.72 mmoles/g) as obtained in the foregoing Synthesis Example 2(1) was added to 200 g of DMSO, and the mixture was stirred for dissolution at 70° C. for 3 hours. Thereafter, 1.66 g (14.4 mmoles) of NHS and 1.38 g (7.2 mmoles) of EDC were added, and the mixture was stirred at 25° C. for 24 hours.

Then, the reaction solution was added dropwise to anhydrous acetone, and a deposit was recovered, washed and dried in vacuo in the same manner as in Synthesis Example 1(3). There was thus prepared active esterified CM hydroxyethyl starch. Z/X and Y/X ratios are as follows.

$$Z/X = 5, Y/X = 10$$

(4) Calculation of Introduction Amount of NHS in Active Esterified Polysaccharide (Polysaccharide Derivative)

The calculation was carried out in the same manner as in the case of active esterified CM dextran as described in Synthesis Example 1(4). An introduction amount of NHS in the active esterified CM hydroxyethyl starch as obtained in Synthesis Example 2(3) was 0.19 mmoles/g.

(5) Self-crosslinking Property of Active Esterified Polysaccharide Derivative

The same test as in the case of active esterified CM dextran as described in Synthesis Example 1(5) was carried out, and the active esterified CM hydroxyethyl starch was judged to be "self-crosslinking".

Synthesis Example 3

(1) Preparation of Raw Material Polysaccharide (Acid Type Polysaccharide)

Carboxymethyl pullulan (acid type CM pulluran) as a raw material polysaccharide, which is a raw material of an active esterified polysaccharide derivative, was prepared.

The preparation was carried out under a condition exactly the same as in Synthesis Example 1(1), except for using pullulan (PU101, manufactured by Hayashibara Biochemical Labs., Inc., weight average molecular weight: 100,000) in place of the dextran as used in Synthesis Example 1(1).

(2) Determination of Carboxyl Group or Carboxymethyl Group

The determination was carried out in the same manner as in the case of acid type CM dextran as described in Synthesis Example 1(2). An amount of the carboxymethyl group of the acid type CM pullulan as obtained in Synthesis Example 3(1) was 0.79 mmoles/g.

(3) Preparation of Active Esterified CM Pullulan

For an active esterification reaction of the acid type CM pullulan, the same reaction solvent, electrophilic group introducing agent and dehydration condensing agent as in Synthesis Example 1(3) were used, thereby preparing an active esterified saccharide.

2.0 g of the acid type CM pullulan (amount of carboxymethyl group: 0.79 mmoles/g) as obtained in the foregoing Synthesis Example 3(1) was added to 200 g of DMSO, and the mixture was stirred for dissolution at 70° C. for 3 hours. Thereafter, 1.82 g (15.8 mmoles) of NHS and 1.51 g (7.9 mmoles) of EDC were added, and the mixture was stirred at 25° C. for 24 hours.

Then, the reaction solution was added dropwise to anhydrous acetone, and a deposit was recovered, washed and dried in vacuo in the same manner as in Synthesis Example 1(3). There was thus prepared active esterified CM pullulan. Z/X and Y/X ratios are as follows.

$Z/X=5, Y/X=10$ (4) Calculation of Introduction Amount of NHS in Active Esterified Polysaccharide (Polysaccharide Derivative)

The calculation was carried out in the same manner as in the case of active esterified CM dextran as described in Synthesis Example 1(4). An introduction amount of NHS in the active esterified CM pullulan as obtained in Synthesis Example 3(3) was 0.20 mmoles/g.

(5) Self-crosslinking Property of Active Esterified Polysaccharide Derivative

The same test as in the case of active esterified CM dextran as described in Synthesis Example 1(5) was carried out, and the active esterified CM pullulan was judged to be "self-crosslinking".

Synthesis Example 4

(1) Preparation of Raw Material Polysaccharide (Acid Type Polysaccharide)

Carboxymethyl dextrin (acid type CM dextrin) as a raw material polysaccharide, which is a raw material of an active esterified polysaccharide derivative, was prepared.

10 g of dextrin (manufactured by Wako Pure Chemical Industries, Ltd., weight average molecular weight: 25,000) was dissolved in 62.5 g of pure water, to which was then added 62.5 g of a 36% (w/v) sodium hydroxide aqueous solution (sodium hydroxide, manufactured by Wako Pure Chemical Industries, Ltd.), and the mixture was stirred for dissolution at 25° C. for 90 minutes.

Thereafter, the addition of 15% monochloroacetic acid, the pH adjustment, the dropwise addition of an ethanol aqueous solution, and the recovery, washing and drying in vacuo of a deposit were carried out in the same manner as in Synthesis Example 1(1). There was thus prepared acid type CM dextrin.

(2) Determination of Carboxyl Group or Carboxymethyl Group

The determination was carried out in the same manner as in the case of acid type CM dextran as described in Synthesis Example 1(2). An amount of the carboxymethyl group of the acid type CM dextrin as obtained in Synthesis Example 4(1) was 1.26 mmoles/g.

(3) Preparation of Active Esterified CM Dextrin

For an active esterification reaction of the acid type CM dextrin, the same reaction solvent, electrophilic group introducing agent and dehydration condensing agent as in Synthesis Example 1(3) were used, thereby preparing an active esterified saccharide.

3.0 g of the acid type CM dextrin (amount of carboxymethyl group: 1.26 mmoles/g) as obtained in the foregoing Synthesis Example 4(1) was added to 90 g of DMSO, and the mixture was stirred for dissolution at 70° C. for 3 hours. Thereafter, 4.35 g (37.8 mmoles) of NHS and 7.22 g (37.8 mmoles) of EDC were added, and the mixture was stirred at 25° C. for 24 hours.

Then, the reaction solution was added dropwise to anhydrous acetone, and a deposit was recovered, washed and dried in vacuo in the same manner as in Synthesis Example 1(3). There was thus prepared active esterified CM dextrin. Z/X and Y/X ratios are as follows.

$Z/X=10, Y/X=10$ (4) Calculation of Introduction Amount of NHS in Active Esterified Polysaccharide (Polysaccharide Derivative)

The calculation was carried out in the same manner as in the case of active esterified CM dextran as described in Synthesis Example 1(4). An introduction amount of NHS in the active esterified CM dextrin as obtained in Synthesis Example 4(3) was 0.80 mmoles/g.

(5) Self-crosslinking Property of Active Esterified Polysaccharide Derivative

The same test as in the case of active esterified CM dextran as described in Synthesis Example 1(5) was carried out, and the active esterified CM dextrin was judged to be "self-crosslinking".

Synthesis Example 5

(1) Preparation of Raw Material Polysaccharide (Acid Type Polysaccharide)

Carboxymethyl highly branched cyclic dextrin (acid type CM highly branched cyclic dextrin) as a raw material polysaccharide, which is a raw material of an active esterified polysaccharide derivative, was prepared.

The preparation was carried out under a condition exactly the same as in Synthesis Example 1(1), except for using highly branched cyclic dextrin (trade name: CLUSTER DEXTRIN, manufactured by Ezaki Glico Co., Ltd., weight average molecular weight: 163,000) in place of the dextran as used in Synthesis Example 4(1).

(2) Determination of Carboxyl Group or Carboxymethyl Group

The determination was carried out in the same manner as in the case of acid type CM dextran as described in Synthesis Example 1(2). An amount of the carboxymethyl group of the acid type CM highly branched cyclic dextrin as obtained in Synthesis Example 5(1) was 1.27 mmoles/g.

(3) Preparation of Active Esterified CM Highly Branched Cyclic Dextrin

For an active esterification reaction of the acid type CM highly branched cyclic dextrin, the same reaction solvent, electrophilic group introducing agent and dehydration condensing agent as in Synthesis Example 1(3) were used, thereby preparing an active esterified saccharide.

3.0 g of the acid type CM highly branched cyclic dextrin (amount of carboxymethyl group: 1.27 mmoles/g) as obtained in the foregoing Synthesis Example 5(1) was added to 90 g of DMSO, and the mixture was stirred for dissolution at 70° C. for 3 hours. Thereafter, 4.38 g (38.1 mmoles) of NHS and 3.64 g (19.05 mmoles) of EDC were added, and the mixture was stirred at 25° C. for 24 hours.

Then, the reaction solution was added dropwise to anhydrous acetone, and a deposit was recovered, washed and dried in vacuo in the same manner as in Synthesis Example 1(3). There was thus prepared active esterified CM highly branched cyclic dextrin. Z/X and Y/X ratios are as follows.

$Z/X=5, Y/X=10$ (4) Calculation of Introduction Amount of NHS in Active Esterified Polysaccharide (Polysaccharide Derivative)

The calculation was carried out in the same manner as in the case of active esterified CM dextran as described in Synthesis Example 1(4). An introduction amount of NHS in the active esterified CM highly branched cyclic dextrin as obtained in Synthesis Example 5(3) was 0.53 mmoles/g.

(5) Self-crosslinking Property of Active Esterified Polysaccharide Derivative

The same test as in the case of active esterified CM dextran as described in Synthesis Example 1(5) was carried out, and the active esterified CM highly branched cyclic dextrin was judged to be "self-crosslinking".

Example 1

Evaluation of Adhesion Prevention in Cecum-abraded Model of Rat

Each of the active esterified polysaccharide derivatives as obtained in the foregoing Synthesis Examples 1 to 5 was provided as an adhesion preventive material for the following experiment.

A Sprague-Dawley (SD) rat was cut and opened up the abdomen under anesthetization with Nembtal; only a cecum was taken out from an incision; a serous membrane on the surface in one side of the cecum was mechanically peeled away by using a surgical knife; and the surface was abraded by using a dry gauze until bleeding was caused. 0.3 mL of the active esterified polysaccharide derivative was coated so as to cover the entire surface of this site, and 0.3 mL of 1 mole $Na_2HPO_4$ was sprayed, gelled and coated on the coated active esterified polysaccharide derivative. Thereafter, the cecum was accommodated in the abdominal cavity such that the incision was positioned just above the coated active esterified polysaccharide derivative, and the incision was sutured. One week and two weeks after the coating application, the abdomen was opened up, and the degree of adhesion on the surface of the cecum was visually observed. Then, a tissue specimen was prepared and histologically studied.

Incidentally, a control was prepared by preparing the same wound site to which, however, was not subjected to coating application. As a result, with respect to the case where the active esterified polysaccharide derivative was subjected to coating application, in all of the samples after one week and two weeks, adhesion between the intestinal wall and the cecum and between the cecum and other internal organ was not caused. In the tissue after one week, the existence of the gel was observed, and wetting of capillary vessels and cells was little. After two weeks, the surface of the cecum was cured and did not change from a normal state so that the sample disappeared.

On the other hand, with respect to the control case, in all of the samples after one week and two weeks, adhesion between the intestinal wall and the cecum and between the cecum and other internal organ was caused; after one week, fibrous substances were histologically observed in the outside of the intestinal tract; and rebirth of capillary vessels and the like was also observed. After two weeks, though the capillary vessels and the like were reduced, the amount of fibrous substances increased, and the fiber density increased so that the formation of strong adhesion was admitted.

INDUSTRIAL APPLICABILITY

The adhesion preventive material comprising a polysaccharide derivative or a polysaccharide composition according to the invention does not utilize a biologically derived material from the safety standpoint and is made up of a natural or artificial saccharide as the major skeleton, and therefore, risks of infectious diseases or the like can be avoided. Toxicity of the component itself or a degradation product thereof is low, and the material is designed so as to have a biodegradable absorption property. Furthermore, since the polysaccharide derivative is small in preparation works to be carried out while previously estimating the time of application so that it is able to rapidly adapt a sudden application and does not require a special device in using it, anyone can simply use it. Then, since the polysaccharide derivative can be provided solely or as a polysaccharide composition containing it, it is applicable to wide and various use methods. The polysaccharide composition does not hinder characteristics of the foregoing polysaccharide derivative.

In addition, the polysaccharide derivative and polysaccharide composition can be processed into various shapes including a powered form, a sheet-like form, and a granular form and can be used for different purposes depending upon the purpose. In using the polysaccharide derivative and the polysaccharide composition, since it is only required to mix necessary reagents, a special device or the like is not required so that the use is simple. In view of the foregoing characteristics, the polysaccharide derivative or its composition is suitable as an adhesion preventive material.

The invention claimed is:

1. A method for preventing biological adhesion comprising the steps of:
    providing an adhesion preventive material comprising a crosslinking dextrin derivative containing at least one active ester group introduced in a dextrin chain, and at least one hydroxyl group, wherein the active ester group of the crosslinking dextrin derivative is capable of reacting with the hydroxyl group of its own molecular chain or with a hydroxyl group of a second molecular chain, wherein the adhesion preventive material does not contain a crosslinking agent,
    forming an ester polymerization material crosslinked due to covalent binding of the active ester group of the crosslinking dextrin derivative and the hydroxyl group of its own molecular chain or the hydroxyl group of the second molecular chain, when the adhesion preventive material is under an alkaline condition, wherein the method is effective to prevent biological adhesion in the biological site.

2. The method according to claim 1, wherein the dextrin derivative is capable of reacting with a hydroxyl group of a biological surface and adhering to the biological surface.

3. The method according to claim 1, wherein the active ester group is an ester group in which an electrophilic group is bound to a carbonyl carbon thereof.

4. The method according to claim 3, wherein the electrophilic group is a group introduced from an N-hydroxyamine based compound.

5. The method according to claim 1, wherein the dextrin derivative contains the active ester group in an amount of from 0.1 to 2 mmoles/g on the basis of the dry weight thereof.

6. The method according to claim 1, wherein the dextrin derivative further contains a carboxyl group and/or a carboxyalkyl group.

7. The method according to claim 6, wherein a raw material dextrin into which the active ester group is introduced is a dextrin which is soluble in an aprotic polar solvent at a temperature between 60° C. and 120° C. in a non-salt type thereof in a precursor stage of the crosslinking dextrin derivative containing a carboxyl group and/or a carboxyalkyl group.

8. The method according to claim 1, wherein the dextrin derivative is of a non-salt type.

9. The method according to claim 1, wherein a raw material dextrin into which the active ester group is introduced is a dextrin which contains neither a carboxyl group nor a carboxyalkyl group by itself.

10. The method according to claim 1, wherein the alkaline condition is in a pH range of from 7.5 to 12.

11. The method according to claim 1, wherein the adhesion preventive material further comprises a polymer other than the cross-linking dextrin derivative.

12. The method according to claim 1, wherein the adhesion preventive material further comprises a pH adjuster in a mixed state with the cross-linking dextrin derivative.

13. The method according to claim 12, wherein the adhesion preventive material further comprises a polymer other than the cross-linking dextrin derivative.

* * * * *